(12) United States Patent
Amemiya

(10) Patent No.: US 7,855,609 B2  
(45) Date of Patent: Dec. 21, 2010

(54) ULTRASONIC TRANSDUCER DRIVING CIRCUIT AND ULTRASONIC DIAGNOSTIC APPARATUS

(75) Inventor: Shinichi Amemiya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 563 days.

(21) Appl. No.: 11/854,903

(22) Filed: Sep. 13, 2007

(65) Prior Publication Data
US 2008/0066552 A1   Mar. 20, 2008

(30) Foreign Application Priority Data
Sep. 15, 2006   (JP)   ............... 2006-251437

(51) Int. Cl.
H03B 5/36   (2006.01)
H01L 41/107   (2006.01)
G01N 29/00   (2006.01)

(52) U.S. Cl. ................ 331/116 FE; 331/116 M; 331/154; 310/318; 600/437

(58) Field of Classification Search ............ 331/116 FE, 331/116 M, 116 R, 154; 310/318; 600/437
See application file for complete search history.

(56) References Cited

U.S. PATENT DOCUMENTS

| | | | |
|---|---|---|---|
| 4,056,761 A | 11/1977 | Jacoby et al. | |
| 4,562,413 A | 12/1985 | Mishiro et al. | |
| 4,563,899 A * | 1/1986 | Nakamura | 73/626 |
| 4,642,581 A | 2/1987 | Erickson | |
| 6,083,164 A * | 7/2000 | Oppelt et al. | 600/437 |
| 6,525,530 B1 | 2/2003 | Jansson et al. | |

FOREIGN PATENT DOCUMENTS

| | | | |
|---|---|---|---|
| JP | 2000-152930 A | * | 6/2000 |
| JP | 2001-245881 A | * | 9/2001 |
| JP | 2004-358133 | | 12/2004 |
| JP | 2006-101997 | | 4/2006 |

* cited by examiner

*Primary Examiner*—Robert Pascal
*Assistant Examiner*—Levi Gannon
(74) *Attorney, Agent, or Firm*—Armstrong Teasdale LLP

(57) ABSTRACT

With the aim of suppressing power consumption and reducing circuit size, a positive FET is turned on in accordance with a positive pulse signal and turned off when a return voltage rises up to a positive threshold. An active ground clamp circuit causes the output line to return to the ground voltage after the elapse of a predetermined period of time. A negative FET is turned on in accordance with a negative pulse signal and turned off when the return voltage falls down to a negative threshold. The active ground clamp circuit causes the output line to return to the ground voltage after the elapse of a predetermined period of time.

15 Claims, 4 Drawing Sheets

ULTRASONIC DIAGNOSTIC APPARATUS
100

ULTRASONIC TRANSDUCER DRIVING CIRCUIT AND ULTRASONIC DIAGNOSTIC APPARATUS

CROSS REFERENCE TO RELATED APPLICATIONS

This application claims the benefit of Japanese Application No. 2006-251437 filed Sep. 15, 2006

BACKGROUND OF THE INVENTION

The present invention relates to an ultrasonic transducer driving circuit and an ultrasonic diagnostic apparatus and, more particularly, relates to an ultrasonic transducer driving circuit and an ultrasonic diagnostic apparatus that can suppress power consumption and allow for a reduction in circuit size.

Heretofore, there is known an ultrasonic diagnostic apparatus including a positive FET (Field Effect Transistor) which outputs a positive voltage onto an output line to an ultrasonic transducer at on state, a negative FET which outputs a negative voltage onto the output line to the ultrasonic transducer, and a driver circuit which drives the positive FET and the negative FET (e.g., see Patent Document 1 and Patent Document 2).

[Patent Document 1] Japanese Unexamined Patent Publication No. 2006-101997 (FIG. 10, FIG. 12, FIG. 14)

[Patent Document 2] Japanese Unexamined Patent Publication No. 2004-358133 (FIG. 2)

In the above ultrasonic diagnostic apparatus of prior art, the output voltage to the ultrasonic transducer can be controlled by adjusting the gate voltages of the FETs (adjusting the voltage drop across each FET).

However, each FET remains on as long as a pulse width duration when a pulse of a voltage is applied to the ultrasonic transducer and this posed a problem of an increase in power consumption.

For this reason, in the above ultrasonic diagnostic apparatus of prior art, power consumption is suppressed by switching the supply voltage to each FET to a low voltage (to reduce the voltage drop across the FET) when the output voltage to the ultrasonic transducer is low.

However, since a supply voltage switching circuit for each FET is a power supply circuit, a problem that the circuit size becomes larger emerged.

SUMMARY OF THE INVENTION

In a first aspect, the present invention provides an ultrasonic transducer driving circuit characterized by comprising: a positive field effect transistor which outputs a positive voltage onto an output line to an ultrasonic transducer at on state; a negative field effect transistor which outputs a negative voltage onto said output line at on state; a ground clamp circuit for causing said output line to return to a ground voltage when said positive field effect transistor and said negative field effect transistor are in off state; and a driver circuit which carries out at least one of the following: turning said positive field effect transistor on in accordance with a positive pulse signal supplied and turning said positive field effect transistor off after the elapse of a period of rise during which said output line rises from the ground voltage up to a predetermined positive voltage; and turning said negative field effect on in accordance with a negative pulse signal supplied and turning said negative field effect transistor off after the elapse of a period of fall during which said output line falls from the ground voltage down to a predetermined negative voltage.

In the ultrasonic transducer driving circuit according to the above first aspect, after the positive field effect transistor is turned on in accordance with the positive pulse signal, at the time of rise to a predetermined positive voltage, the positive field effect transistor is turned off; therefore, the output voltage to the ultrasonic transducer rises, but is restricted up to the predetermined positive voltage. Then, the output voltage to the ultrasonic transducer can be returned to the ground voltage by the ground clamp circuit. Thus, both the voltage value and the pulse width of a positive pulse that is applied to the ultrasonic transducer can be controlled. Also, after the negative field effect transistor is turned on in accordance with the negative pulse signal, at the time of fall to a predetermined negative voltage, the negative field effect transistor is turned off; therefore, the output voltage to the ultrasonic transducer falls, but is restricted down to the predetermined negative voltage. Then, the output voltage to the ultrasonic transducer can be returned to the ground voltage by the ground clamp circuit. Thus, both the voltage value and the pulse width of a negative pulse that is applied to the ultrasonic transducer can be controlled. Because each FET is turned off when the output voltage to the ultrasonic transducer goes up to a predetermined voltage or goes down to a predetermined voltage, power consumption can be suppressed. Because there is no need for supply voltage switching circuits for the FETs, circuit size can be reduced.

In a second aspect, the present invention provides an ultrasonic transducer driving circuit characterized in that said driver circuit in the ultrasonic transducer driving circuit according to said first aspect drives said positive field effect transistor and said negative field effect transistor based on said positive pulse signal, said negative pulse signal, and a return voltage returned from said output line.

In the ultrasonic transducer driving circuit according to the above second aspect, control is performed using the return voltage returned from the output line; thus, the output voltage to the ultrasonic transducer can be controlled accurately even if there is variation in the circuit elements.

In a third aspect, the present invention provides an ultrasonic transducer driving circuit characterized in that said driver circuit in the ultrasonic transducer driving circuit according to said second aspect comprises a positive drive circuit which drives said positive field effect transistor and a negative drive circuit which drives said negative field effect transistor.

In the ultrasonic transducer driving circuit according to the above third aspect, the positive driver circuit and the negative driver circuit are separate; thus, each respective logic circuit becomes easy to construct.

In a forth aspect, the present invention provides an ultrasonic transducer driving circuit characterized in that said positive drive circuit in the ultrasonic transducer driving circuit according to said third aspect includes: a positive comparator which compares a positive threshold with said return voltage; and a positive logic circuit which outputs a drive signal for said positive field effect transistor based on said positive pulse signal and an output voltage of said positive comparator.

In the ultrasonic transducer driving circuit according to the above fourth aspect, a positive output voltage to the ultrasonic transducer can be adjusted by adjusting the positive threshold.

In a fifth aspect, the present invention provides an ultrasonic transducer driving circuit characterized in that said positive logic circuit in the ultrasonic transducer driving circuit according to said fourth aspect is a flip-flop circuit.

In the ultrasonic transducer driving circuit according to the above fifth aspect, after the positive field effect transistor is turned off when the output line rises from the ground voltage to the predetermined positive voltage, the off state of the positive field effect transistor can be maintained even if the voltage on the output line falls.

In a sixth aspect, the present invention provides an ultrasonic transducer driving circuit characterized in that said native drive circuit in the ultrasonic transducer driving circuit according to any of said third through fifth aspects includes: a negative comparator which compares a negative threshold with said return voltage; and a negative logic circuit which outputs a drive signal for said negative field effect transistor based on said negative pulse signal and an output voltage of said negative comparator.

In the ultrasonic transducer driving circuit according to the above sixth aspect, a negative output voltage to the ultrasonic transducer can be adjusted by adjusting the negative threshold.

In a seventh aspect, the present invention provides an ultrasonic transducer driving circuit characterized in that said negative logic circuit in the ultrasonic transducer driving circuit according to said sixth aspect is a flip-flop circuit.

In the ultrasonic transducer driving circuit according to the above seventh aspect, after the negative field effect transistor is turned off when the output line falls from the ground voltage to the predetermined negative voltage, the off state of the negative field effect transistor can be maintained even if the voltage on the output line rises.

In an eighth aspect, the present invention provides an ultrasonic diagnostic apparatus characterized by comprising: an ultrasonic probe; an ultrasonic transducer driving circuit according to any of said first through seventh aspects; a pulser means which supplies said positive pulse signal, said negative pulse signal, said positive threshold, and said negative threshold to said ultrasonic transducer driving circuit; a receiver means which receives echo signals acquired at said ultrasonic probe and outputs an acoustic beam signal; an image generating means which generates an ultrasonic image based on said acoustic beam signal: and a display means which displays said ultrasonic image.

In the ultrasonic diagnostic apparatus according to the above eighth aspect, power consumption can be suppressed and circuit size can be reduced because of use of the ultrasonic transducer driving circuit in any of said first through seventh aspects.

According to the ultrasonic transducer driving circuit and the ultrasonic diagnostic apparatus of the present invention, power consumption can be suppressed. Besides, circuit size can be reduced.

The ultrasonic transducer driving circuit and the ultrasonic diagnostic apparatus of the present invention can be utilized to improve the performance of ultrasonic diagnostic apparatus and reduce the size thereof.

Further objects and advantages of the present invention will be apparent from the following description of the preferred embodiments of the invention as illustrated in the accompanying drawings.

DETAILED DESCRIPTION OF THE INVENTION

Figure 1:
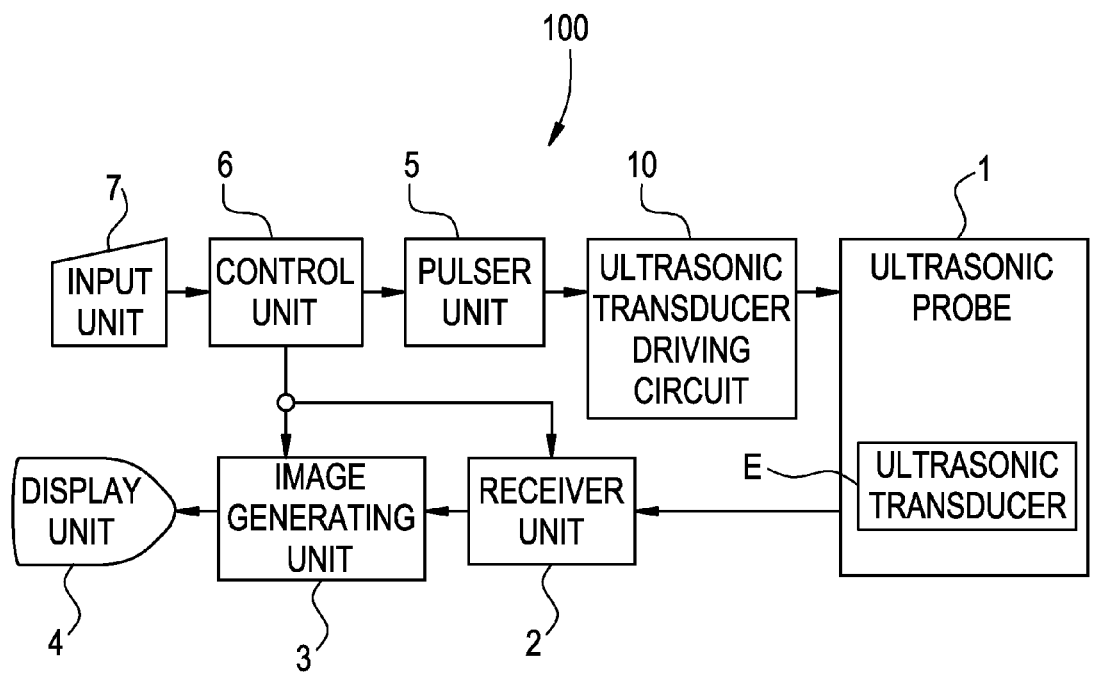
FIG. 1 is a block diagram showing an ultrasonic diagnostic apparatus relevant to Embodiment 1.

In the following, the present invention will be described in more detail by way of its embodiments that are shown in the drawings. These embodiments are not intended to limit the present invention.

Embodiment 1

FIG. 1 is a structural diagram showing an ultrasonic diagnostic apparatus 100 relevant to Embodiment 1.

This ultrasonic diagnostic apparatus 100 includes: an ultrasonic probe 1 within which multiple ultrasonic transducers E are installed and which transmits ultrasonic beams from the transducers into a specimen body and receives ultrasonic echoes from within the specimen body; a receiver unit 2 which generates and outputs an acoustic beam signal from the ultrasonic echoes; an image generating unit 3 which generates an ultrasonic image based on the acoustic beam signal; a display unit 4 which displays the ultrasonic image; an ultrasonic transducer driving circuit 10 which drives the ultrasonic transducer E for transmitting the ultrasonic pulses; a pulser unit 5 which inputs a signal for transmission to the ultrasonic transducer driving circuit 10; a control unit 6 which takes overall control of the apparatus; and an input unit 7 which is used for an operator to operate the apparatus.

Figure 2:
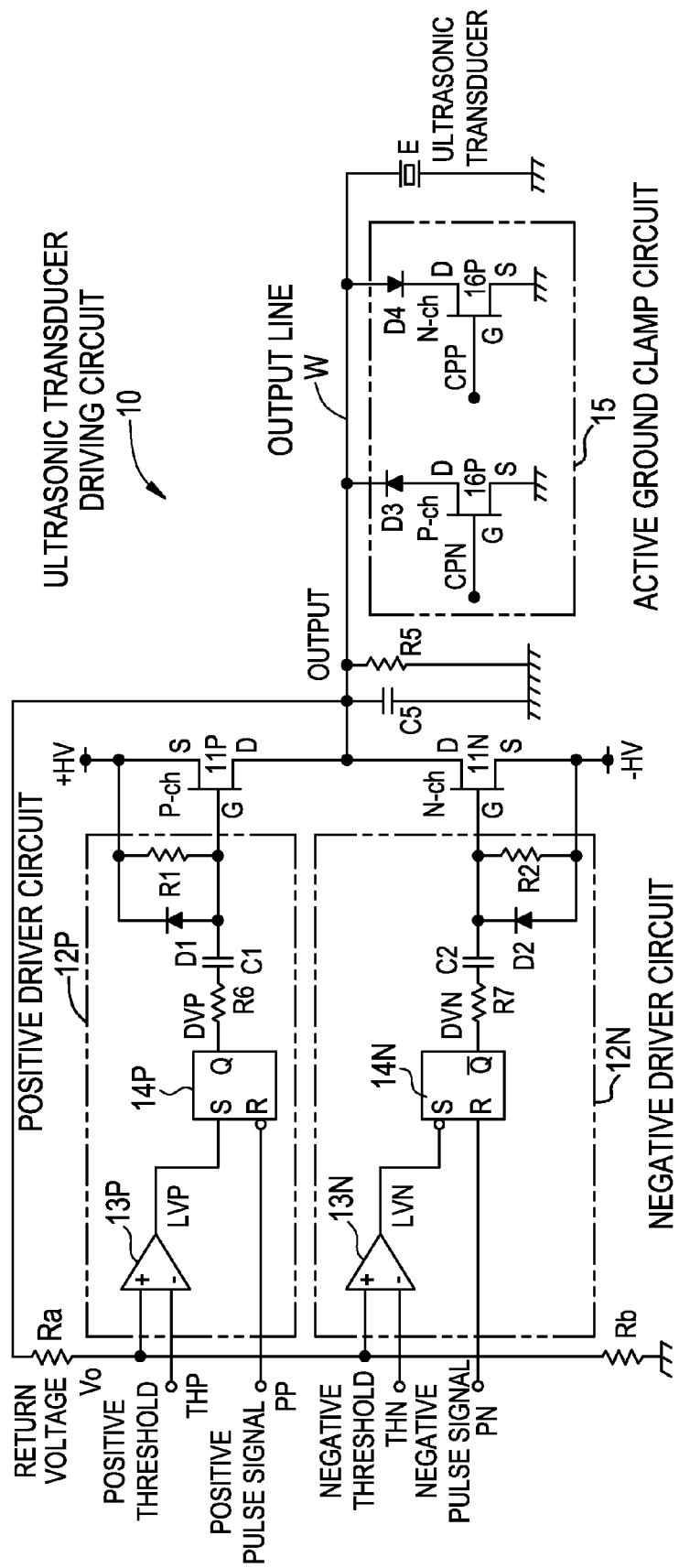
FIG. 2 is a circuit diagram showing an ultrasonic transducer driving circuit relevant to Embodiment 1.

FIG. 2 is a circuit diagram showing the ultrasonic transducer driving circuit 10 relevant to Embodiment 1.

The ultrasonic transducer driving circuit 10 comprises: a positive FET 11P which outputs a positive voltage +HV onto an output line W to the ultrasonic transducer E at on state; a negative FET 11N which outputs a negative voltage −HV onto the output line W at on state; a positive driver circuit 12P which drives the positive FET 11P based on a positive pulse signal PP and a positive threshold THP supplied from the pulser unit 5 and a return voltage Vo returned from the output line W; a negative driver circuit 12N which drives the negative FET 11N based on a negative pulse signal PN and a negative threshold THN supplied from the pulser unit 5 and the return voltage Vo; and an active ground clamp circuit 15.

The positive driver circuit 12P includes: a comparator 13P which outputs a positive comparison signal LVP being "H" when the return voltage Vo is higher than the positive threshold THP and "L" otherwise; and a flip-flop 14P whose output Q shifts to "L" at the "falling edge H to L" of the positive pulse signal PP and shifts to "H" at the "rising edge L to H" of the positive comparison signal LVP.

The negative driver circuit 12N includes: a comparator 13N which outputs a negative comparison signal LVN being "H" when the return voltage Vo is higher than the negative threshold THN and "L" otherwise; and a flip-flop 14N whose inverted output Qbar shifts to "H" at the "rising edge: L to H" of the negative pulse signal PP and shifts to "L" at the "falling edge: H to L" of the negative comparison signal LVN.

The active ground clamp circuit 15 comprises a positive FET 16P and a negative FET 16N which act to cause the output line W to return to the ground voltage at on state.

Resistors R5, R6, R7, and a capacitor C5 which are shown in FIG. 2 are added to make the output response later than the return response and stabilize the operation, but they are omissible if sufficient operation is ensured by the essential components of the circuit.

Figure 3:
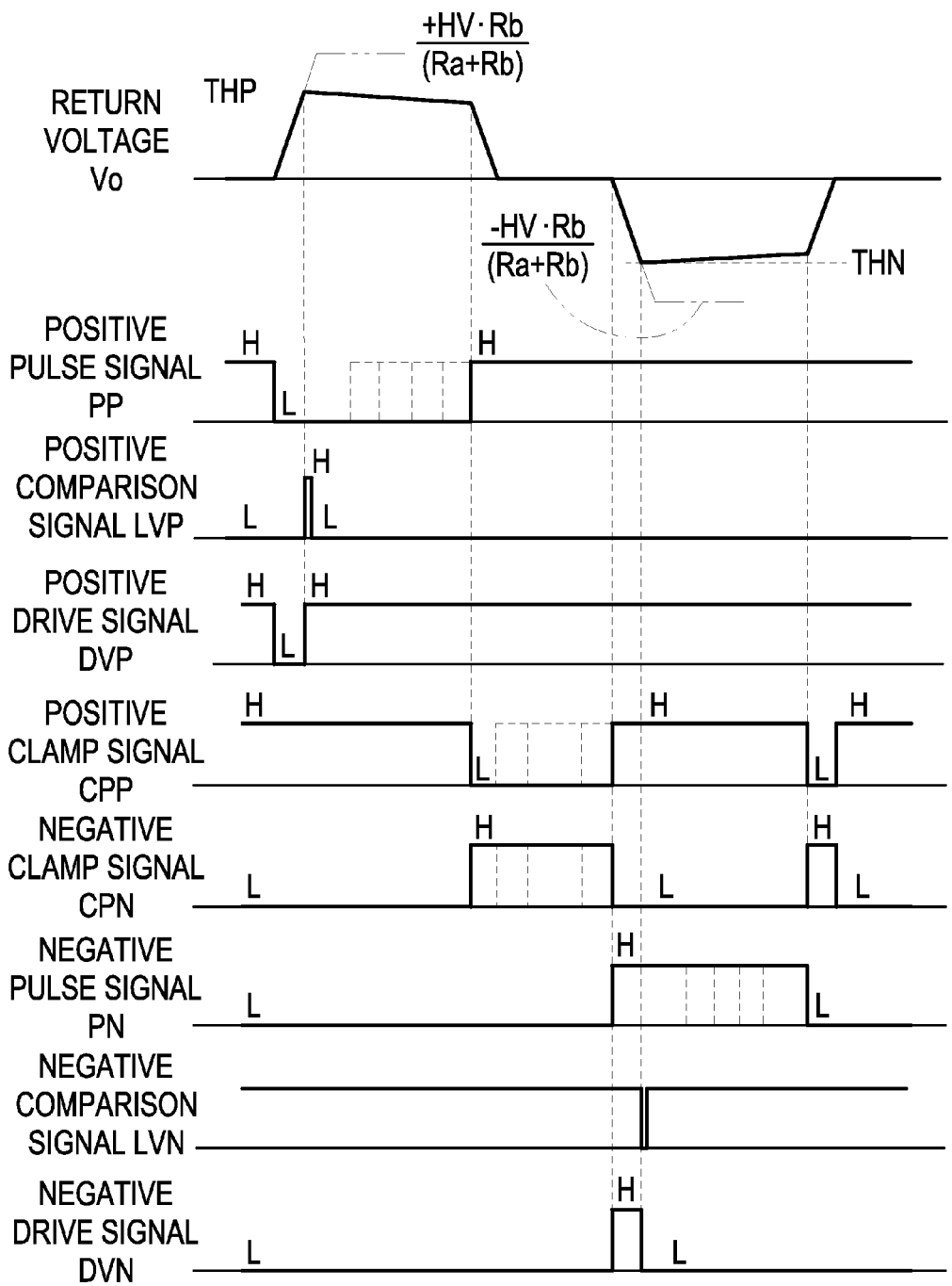
FIG. 3 is a timing chart for a period in which a predetermined positive voltage is applied to an ultrasonic transducer, followed by a return to the ground voltage and application of a predetermined negative voltage.

FIG. 3 is a timing chart for a period in which a predetermined positive voltage is applied to the ultrasonic transducer E, followed by a return to the ground voltage and application of a predetermined negative voltage.

When the positive pulse signal PP shifts from "H to L", at the falling edge of the positive pulse signal PP, the output Q of the flip-flop 14P, namely, a positive drive signal DVP shifts from "H to L". Then, the gate voltage of the positive FET 11P falls with a fixed time constant (determined by R1, R6, C1), the output voltage to the output line W rises from the ground voltage with a fixed time constant, and the return voltage Vo also rises from the ground voltage with a fixed time constant. When the return voltage Vo goes up to the positive threshold THP, the positive comparison signal LVP shifts from "L to H". At the rising edge of the positive comparison signal LVP, the output Q of the flip-flop 14P, namely, the positive drive signal DVP shifts from "L to H". Then, the gate voltage of the positive FET 11P rises with a fixed time constant (determined by R6 and C1), but the output voltage to the output line W is maintained substantially at THP·Rb/(Ra+Rb) because the time constant of the output line W (determined by floating capacitance and R5, C5, and the like) is large. On the elapse of a predetermined period of time, the active ground clamp circuit 15 returns the output line W to the ground voltage by a positive clamp signal CPP and a negative clamp signal CPN. In the manner described above, a positive pulse is applied to the ultrasonic transducer E, with the voltage of the pulse being controlled by the positive threshold THP and the pulse width being controlled by the positive pulse signal PP and the clamp signals CPP, CPN.

Next, when the negative pulse signal PN shifts from "L to H", at the rising edge of the negative pulse signal PN, the inverted output Qbar of the flip-flop 14P, namely, a negative drive signal DVN shifts from "L to H". Then, the gate voltage of the negative FET 11N falls with a fixed time constant (determined by R2, R7, C2), the output voltage to the output line W falls from the ground voltage with a fixed time constant, and the return voltage Vo also falls from the ground voltage with a fixed time constant. When the return voltage Vo goes down to the negative threshold THN, the negative comparison signal LVN shifts from "H to L". At the falling edge of the negative comparison signal LVN, the inverted output Qbar of the flip-flop 14N, namely, the negative drive signal DVN shifts from "H to L". Then, the gate voltage of the negative FET 11N rises with a fixed time constant (determined by R7 and C2), but the output voltage to the output line W is maintained substantially at −THN·Rb/(Ra+Rb) because the time constant of the output line W (determined by floating capacitance and R5, C5, and the like) is large. On the elapse of a predetermined period of time, the active ground clamp circuit 15 returns the output line W to the ground voltage by the positive clamp signal CPP and the negative clamp signal CPN. In the manner described above, a negative pulse is applied to the ultrasonic transducer E, with the voltage of the pulse being controlled by the negative threshold THN and the pulse width being controlled by the negative pulse signal PP and the clamp signals CPP, CPN.

Figure 4:
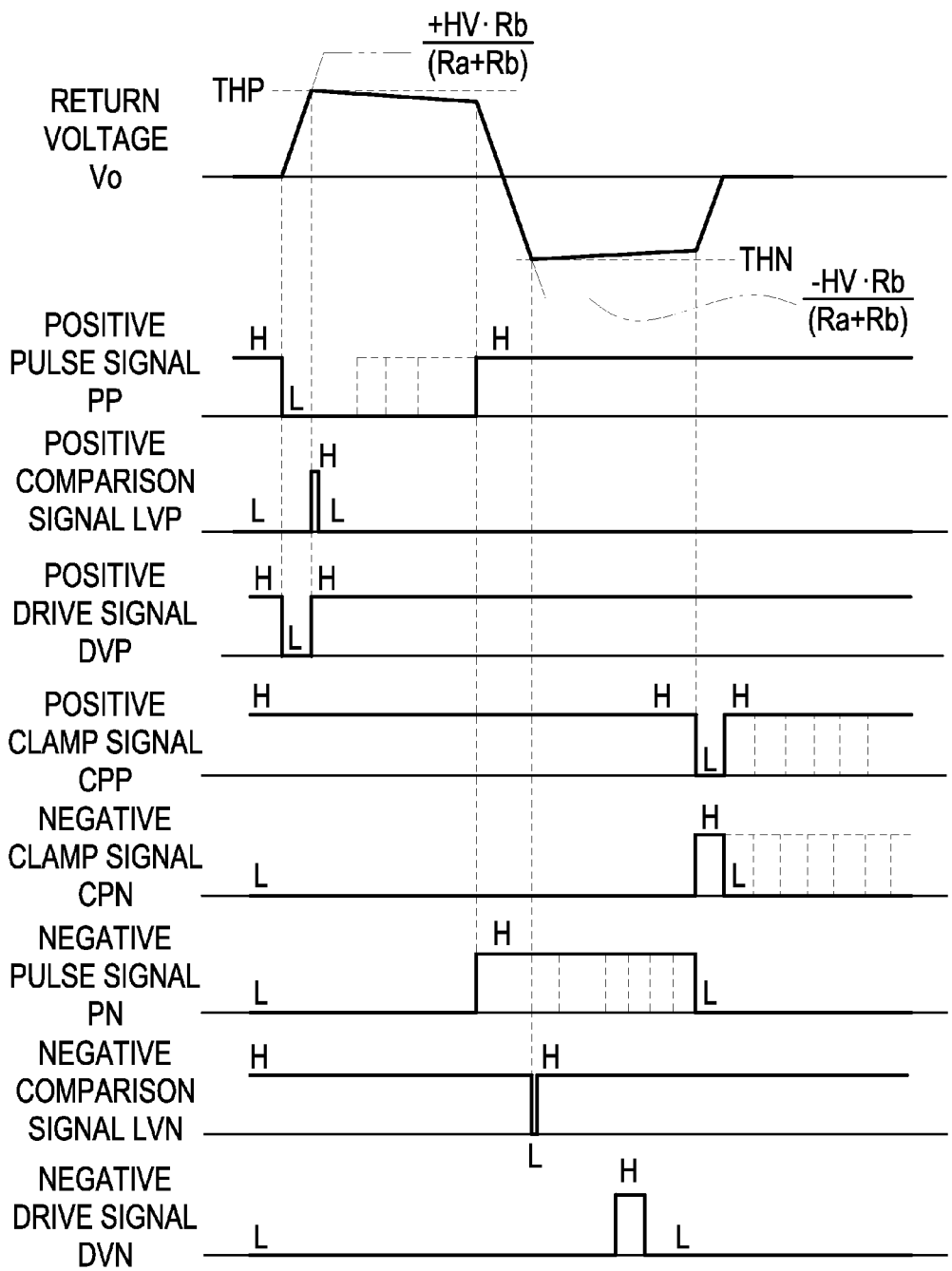
FIG. 4 is a timing chart for a period in which the predetermined positive voltage is applied to the ultrasonic transducer, followed by application of the predetermined negative voltage.

FIG. 4 is a timing chart for a period in which the positive voltage +HV is applied to the ultrasonic transducer E, followed by application of the negative voltage −HV.

In this case, the pulse width of a positive pulse is controlled by the positive pulse signal PP and the negative pulse signal PN According to the ultrasonic transducer driving circuit 10 and the ultrasonic transducer driving circuit 100 of Embodiment 1, the following advantageous effects can be obtained.

(1) Power consumption can be suppressed, because the FET 11P or 11N is turned off when the output voltage to the ultrasonic transducer E goes up to a predetermined voltage or goes down to a predetermined voltage.

(2) The circuit size can be reduced, because there is no need for supply voltage switching circuits for the FETs 11P and 11N.

(3) The voltage of a pulse that is applied to the ultrasonic transducer E can be controlled accurately.

Embodiment 2

The present invention can be applied in the same manner as for Embodiment 1, when a predetermined negative voltage is applied to the ultrasonic transducer E, followed by a return to the ground voltage and application of a predetermined positive voltage, and even when the predetermined negative voltage is applied to the ultrasonic transducer E, followed by application of the predetermined positive voltage.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasonic transducer driving circuit comprising:
a positive field effect transistor which outputs a positive voltage onto an output line to an ultrasonic transducer at on state;
a negative field effect transistor which outputs a negative voltage onto said output line at on state;
a ground clamp circuit for causing said output line to return to a ground voltage when said positive field effect transistor and said negative field effect transistor are in off state; and
a driver circuit which carries out at least one of the following: turning said positive field effect transistor on in accordance with a positive pulse signal supplied and turning said positive field effect transistor off after the elapse of a period of rise during which said output line rises from the ground voltage up to a predetermined positive voltage; and turning said negative field effect transistor on in accordance with a negative pulse signal supplied and turning said negative field effect transistor off after the elapse of a period of fall during which said output line falls from the ground voltage down to a predetermined negative voltage, wherein said driver circuit drives said positive field effect transistor and said negative field effect transistor based on said positive pulse signal, said negative pulse signal, and a return voltage returned from said output line.

2. The ultrasonic transducer driving circuit according to claim 1, wherein said driver circuit comprises a positive drive circuit which drives said positive field effect transistor and a negative drive circuit which drives said negative field effect transistor.

3. The ultrasonic transducer driving circuit according to claim 2, wherein said positive drive circuit includes: a positive comparator which compares a positive threshold with said return voltage; and a positive logic circuit which outputs a drive signal for said positive field effect transistor based on said positive pulse signal and an output voltage of said positive comparator.

4. The ultrasonic transducer driving circuit according to claim 3, wherein said positive logic circuit is a flip-flop circuit.

5. The ultrasonic transducer driving circuit according to claim 4, wherein said negative drive circuit includes: a negative comparator which compares a negative threshold with said return voltage; and a negative logic circuit which outputs a drive signal for said negative field effect transistor based on said negative pulse signal and an output voltage of said negative comparator.

6. The ultrasonic transducer driving circuit according to claim 3, wherein said negative drive circuit includes: a negative comparator which compares a negative threshold with said return voltage; and a negative logic circuit which outputs a drive signal for said negative field effect transistor based on said negative pulse signal and an output voltage of said negative comparator.

7. The ultrasonic transducer driving circuit according to claim 6, wherein said negative logic circuit is a flip-flop circuit.

8. The ultrasonic transducer driving circuit according to claim 2, wherein said negative drive circuit includes: a negative comparator which compares a negative threshold with said return voltage; and a negative logic circuit which outputs a drive signal for said negative field effect transistor based on said negative pulse signal and an output voltage of said negative comparator.

9. The ultrasonic transducer driving circuit according to claim 8, wherein said negative logic circuit is a flip-flop circuit.

10. An ultrasonic diagnostic apparatus comprising:
an ultrasonic probe;
an ultrasonic transducer driving circuit comprising:
a positive field effect transistor which outputs a positive voltage onto an output line to said ultrasonic probe at on state;
a negative field effect transistor which outputs a negative voltage onto said output line at on state;
a ground clamp circuit for causing said output line to return to a ground voltage when said positive field effect transistor and said negative field effect transistor are in off state; and
a driver circuit that drives said positive field effect transistor and said negative field effect transistor based on a positive pulse signal, a negative pulse signal, and a return voltage returned from said output line;
a pulser device which supplies said positive pulse signal, said negative pulse signal, a positive threshold, and a negative threshold to said ultrasonic transducer driving circuit;
a receiver device which receives echo signals acquired at said ultrasonic probe and outputs an acoustic beam signal;
an image generating device which generates an ultrasonic image based on said acoustic beam signal; and
a display device which displays said ultrasonic image.

11. An ultrasonic diagnostic apparatus according to claim 10, wherein said ultrasonic transducer driving circuit comprises a positive drive circuit which drives said positive field effect transistor and a negative drive circuit which drives said negative field effect transistor.

12. An ultrasonic diagnostic apparatus according to claim 11, wherein said positive drive circuit includes: a positive comparator which compares said positive threshold with said return voltage; and a positive logic circuit which outputs a drive signal for said positive field effect transistor based on said positive pulse signal and an output voltage of said positive comparator.

13. An ultrasonic diagnostic apparatus according to claim 12, wherein said positive logic circuit is a flip-flop circuit.

14. An ultrasonic diagnostic apparatus according to claim 11, wherein said negative drive circuit includes: a negative comparator which compares said negative threshold with said return voltage; and a negative logic circuit which outputs a drive signal for said negative field effect transistor based on said negative pulse signal and an output voltage of said negative comparator.

15. An ultrasonic diagnostic apparatus according to claim 14, wherein said negative logic circuit is a flip-flop circuit.

* * * * *